(12) United States Patent
Nydén et al.

(10) Patent No.: US 7,662,222 B2
(45) Date of Patent: Feb. 16, 2010

(54) METHOD AND USE OF NANOPARTICLES TO BIND BIOCIDES IN PAINTS

(75) Inventors: Magnus Nydén, Billdal (SE); Camilla Fant, Kullavik (SE)

(73) Assignee: I-Tech AB, Gothenburg (SE)

( * ) Notice: Subject to any disclaimer, the term of this patent is extended or adjusted under 35 U.S.C. 154(b) by 0 days.

(21) Appl. No.: 12/456,775

(22) Filed: Jun. 23, 2009

(65) Prior Publication Data

US 2009/0270357 A1 Oct. 29, 2009

Related U.S. Application Data

(62) Division of application No. 11/827,466, filed on Jul. 12, 2007, now abandoned, which is a division of application No. 11/373,661, filed on Mar. 10, 2006, now Pat. No. 7,311,766.

(60) Provisional application No. 60/661,083, filed on Mar. 11, 2005.

(51) Int. Cl.
C09D 5/16 (2006.01)
A01N 43/48 (2006.01)
A01N 43/50 (2006.01)
A01N 31/00 (2006.01)
A01N 33/00 (2006.01)

(52) U.S. Cl. .............. 106/18.32; 106/15.05; 106/18.33; 106/18.35; 106/18.36; 424/78.09; 424/405; 424/635; 424/638; 424/641; 424/722; 428/402; 428/403; 428/404; 514/63; 514/184; 514/191; 514/241; 514/396; 514/408; 514/494; 514/499; 514/500; 514/588; 514/595; 514/596; 514/600; 514/740; 514/741; 514/772; 523/122; 523/177

(58) Field of Classification Search .............. 106/15.05, 106/18.32, 18.33, 18.35, 18.36; 424/78.09, 424/405, 635, 638, 641, 691, 722; 428/402, 428/403, 404; 514/63, 184, 191, 241, 396, 514/408, 494, 499, 500, 588, 595, 596, 600, 514/740, 741, 772; 523/122, 177

See application file for complete search history.

(56) References Cited

U.S. PATENT DOCUMENTS 6,762,227 B1 * 7/2004 Elwing et al. ............... 524/106
7,311,766 B2 12/2007 Nyden et al.
2006/0084278 A1 4/2006 Winter et al.

\* cited by examiner

*Primary Examiner*—Anthony J Green
(74) *Attorney, Agent, or Firm*—Lynn E. Barber

(57) ABSTRACT

This invention relates to the use of a combination of selected substances in paint to prevent the settlement and growth of different biofouling organisms with a reduced negative effect on the ecosystems compared to present methods.

6 Claims, 6 Drawing Sheets

Figure 1.
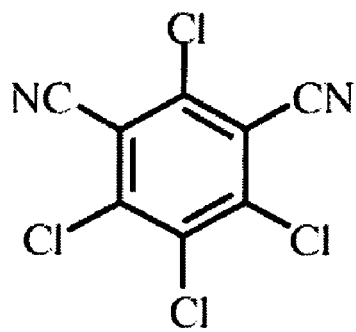 a)
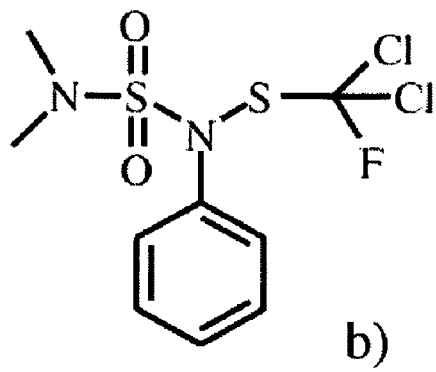 b)
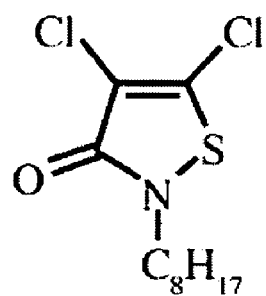 c)
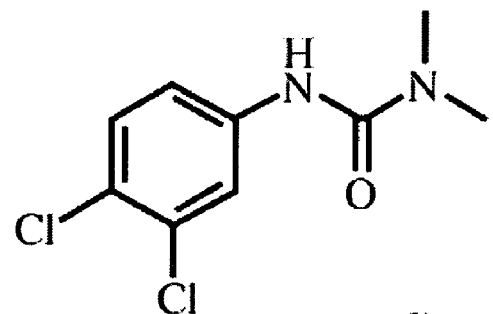 d)
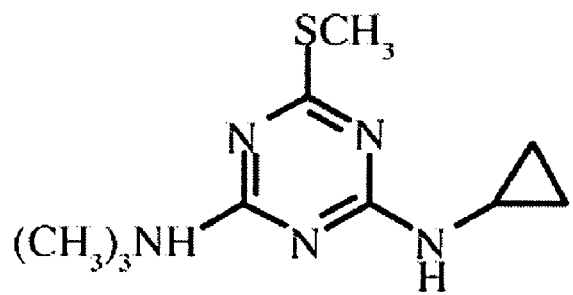 e)
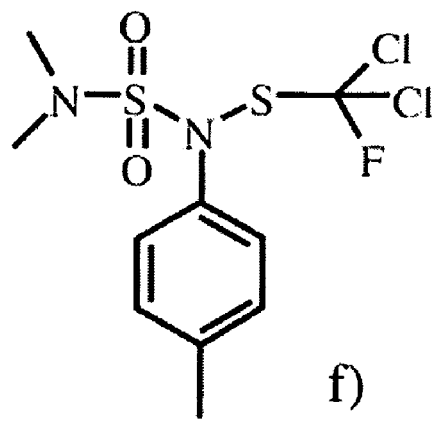 f)

Figure 2 a + b.
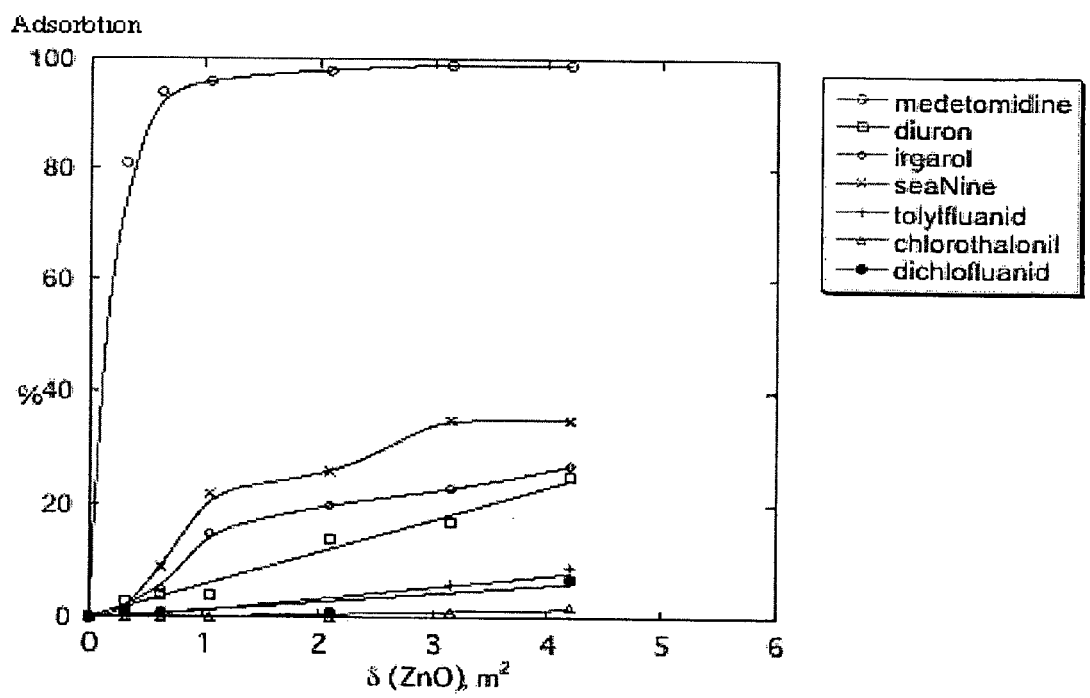
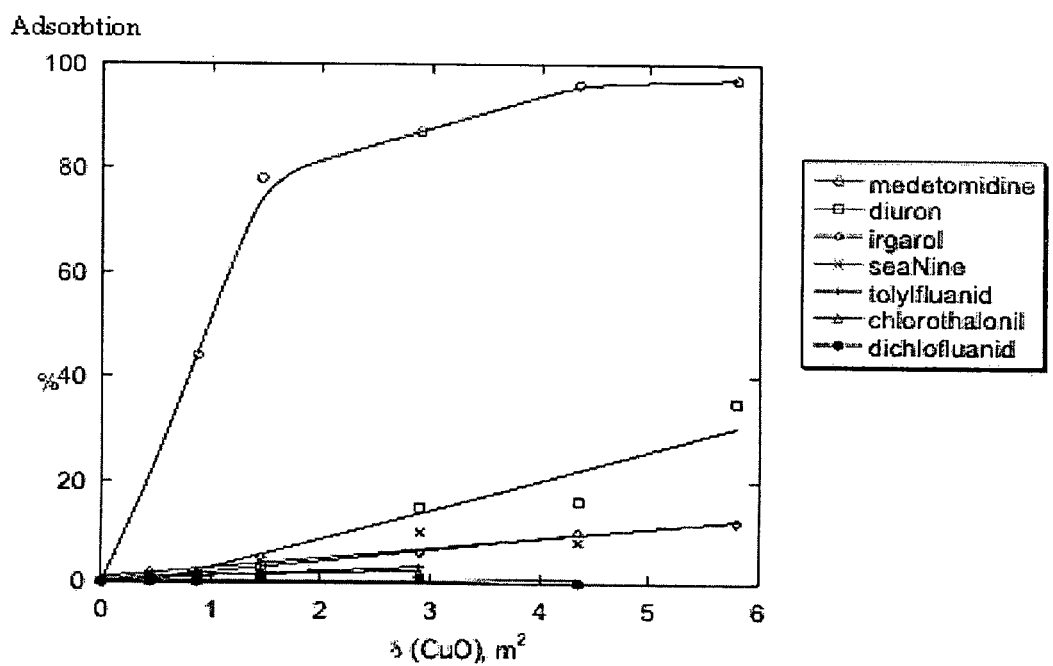

METHOD AND USE OF NANOPARTICLES TO BIND BIOCIDES IN PAINTS

CROSS-REFERENCE TO RELATED APPLICATIONS

This application is a divisional application of U.S. Ser. No. 11/827,466 filed Jul. 12, 2007, now abandoned, which is a divisional application of U.S. Ser. No. 11/373,661 filed Mar. 10, 2006, issued on Dec. 25, 2007 as U.S. Pat. No. 7,311,766 which claims priority from U.S. provisional application Ser. No. 60/661,083 filed Mar. 11, 2005, all of which are incorporated herein by reference.

BACKGROUND OF THE INVENTION

1. Field of the Invention

The invention herein relates to the method and use in an antifouling paint of an imidazole containing compound, such as Medetomidine, bound to metal nanoparticles to develop an efficient antifouling surface and improve the performance of antifouling paints with regard to distributed fixation of the biocide in the paint matrix for even release and effect in hindering, for example, barnacle colonization. Other biocide systems can be used with the same metal nano particle interaction for even release in other paints than marine antifouling paint.

2. Description of the Related Art

The growth of biofouling organisms on underwater structures is a costly and hazardous problem in both marine and freshwater applications. The presence of fouling organisms such as barnacles, algae, tube worms and the like causes economic damage in various ways: for example attachment to the hulls of ships reduces fuel efficiency and causes loss of profitable time because of the need to clean the hulls. Similarly, the attachment of these organisms to cooling water equipment decreases heat conductivity, which eventually reduces the cooling power of the equipment and drives up costs. Also other marine industries and installations, e.g. aqua culture equipment and oil/gas off-shore installations and plants have significant problems with marine biofouling.

Mechanical cleaning of marine surfaces has been introduced as an alternative to toxides and biocides. Notably, water jet cleaning and mechanical cleaning using brushes are in use. The majority of these methods are, however, work-intensive and therefore expensive.

The most efficient antifouling paints have been "self-polishing copolymer" paints based on a polymeric binder to which biocidal organotin, in particular tributylin are chemically bound and from which biocidal organotin is gradually hydrolyzed by seawater as described for example in UK patent GB-A-1457590. These organotin copolymer paints prevent fouling by releasing the organotin compounds during hydrolysis of the polymer. The outermost paint layer becomes depleted of biocides and is swept of the surface of the hull by the movement of the ship through water. Organotin copolymer paints also contain copper oxide pigment which is effective against biofouling against marine organisms while the tributylin acts as a protection from slime and weed.

Paint containing organotin compounds, in particular tributylin have proven to cause negative environmental consequences, harming sea life, causing deformations in oysters and sex changes in whelks. It have been noted that organotin compounds are degraded slowly, and as a consequence these compounds have been accumulated in the sediments in localized areas. Several countries and international organizations have therefore introduced restrictions and prohibitions over their use and further restrictions are expected. Sale and application of tributylin antifouling is to cease, under the International Maritime Organization (IMO) Antifouling System Convention agreed in October 2001. The treaty calls for the ban on application from 1st of January 2003 and total prohibition on hulls by 1st of January 2008.

With the recent restrictions on the use of these toxic coatings in many countries, the boat and ship owners have fallen back to the technically inferior but less toxic copper oxide based coatings. The life of copper oxide based coatings rarely exceeds 2 years in normal fouling conditions compared to 5 years with self-polishing tributylin. Dissatisfaction existed because copper oxide based coatings did not satisfy the boat and ship operators and owners. Neither did it satisfy environmental protection organizations because of its toxicity to the environment. When the copper compounds are used in reduced concentrations for ecological reasons these paints need however booster biocides against barnacles and algae to achieve performance acceptable for ship owners and other types of marine industries.

Recent progress within the field of self-polishing paints includes the use of a zinc acrylate copolymer utilizing ion exchange as the release mechanism.

Concern for the possible effects of antifoulant toxicants on the environment has encouraged the development and use of systems which attempt to control fouling through surface modifications; for example, prevention of attachment through the use of silicone or fluorine containing polymers having non-stick or release properties, described for example in the following patent documents WO-0014166A1, US92105410, JP53113014, US92847401, DE2752773, EP874032A2, and EP 885938A2. It has been shown that these paints tend to be fragile, resulting in cracking and peeling of the surface.

A new alternative technology was introduced early in the 1990s. Although this was also said to be self-polishing technology, the process to obtain this was no longer through hydrolysis of a polymer. Instead combinations of different water sensitive and partly water soluble binders such as rosin, alone or mixed with acrylates as described in e.g. European patent EP0289481, EP526441 were used. The experience has shown that these paints have not been able to provide the same high and reliable performance as the hydrolyzing organotin-based paints.

Lately new polymers have been developed, based on the same principles as the organotin polymers, i.e. hydrolysis of an insoluble polymer to provide a slightly water soluble product. Among these are e.g. the self-polishing polymers described in WO8402915. Instead of incorporating organotin groups in the polymer chain, this describes the incorporation of organosilyl groups. Experience has shown that these paints have many of the properties associated with the organotin copolymer technology. However, it has also been found that over a long period cracking and peeling on the surface these paints may occur. This is caused by the leaching of soluble components, resulting in the formation of a residual layer that has a different composition than the original paint.

An approach to solve this has been to modify the silyl polymer with different co-monomers, described in EP0646630, EP1016681 and EP1127902. Another approach has been to include fibres to strengthen and increase the cohesive strength in the whole paint and particularly all the residual layer formed as described in WO0077102. A third approach has been to develop a paint wherein mixtures of organosilyl copolymers and rosin have been used to reduce the build up of this residual layer. This has been described in EP0802243. The use of low molecular plasticizers, more specifically chloroparaffines, has also been employed. This is described in EP0775733.

Along the Swedish west coast as well as along the coasts of the North Atlantic Ocean, barnacles and algae are an economic and technical problem. The fully grown barnacle is a stationary crustacean, characterized by a centimeter sized cone shape and enclosing layers of calcinous plates. The mechanical strength of the animal's attachment to solid surfaces is very high, which is why it is difficult to mechanically remove barnacles from solid surface. The animal undergoes different development stages as free-swimming larvae, where the last larva stage is referred to as the cyprid stage. The cyprid screens solid surfaces suitable for settling with the help of a nervous protuberance. In connection with settling, the "settling-glue" referred to as balanus cement is secreted from specialized glands localized to the protuberance and the animal thereby settles to the solid surface. After settlement the animal undergoes a metamorphosis into an adult and stationary animal. When using an old copper leaking paint, with high concentration of copper, one of the first organisms to foul is barnacles.

Algae are also relatively insensitive to copper and the amount of leaking copper needed to inhibit fouling of algae is high. Therefore, copper-containing marine antifouling paints are "boosted" by some manufacturers with more specific algicides. The algicides inhibit the zoospores to attach or inhibit the photosynthesis. Both methods give the result of reduced algae fouling.

A future antifouling paint, boosted with a biocide, should act with high specificity i.e. only target fouling organisms being affected, leaving other marine mechanisms unharmed. The paint should also be designed to attain a controlled release of the active substance. An efficient approach to accomplish a controlled release is by the formation of a bond to a large molecule. Due to a large size and low mobility of a large molecule the biocide diffusion through the paint film can be restricted and thereby have a release rate which is only dependent on the polishing rate of the self-polishing paint. Furthermore the biodegradation of the antifouling agent is another important aspect in order to prevent accumulation in water and sediments and thus affecting the marine environment rather than the target biofouling organism alone.

Several compounds have been presented with antifouling activity. Among those compounds are pharmacological agents with known pharmacological profiles in vertebrates. It has been reported that a selection of pharmacological compounds, that act upon serotonin and dopamine neurotransmitters has the ability to either impede or promote the attachment of barnacles. Serotonine antagonists, such as Cyproheptadine and Ketanserin, and dopamine agonists, such as R (−)-NPA and (+)-Bromocriptine, have exhibited inhibitory properties. Another pharmacological agent that has proven to be an efficient inhibitor with regards to barnacle settlement is the highly selective alpha2-adrenoreceptor agonist Medetomidine or (S,R)-4(5)-[1-(2,3-dimethylphenyl)ethyl]-1H-imidazole. The larval settlement is impeded already at low concentrations, 1 nM to 10 nM. Medetomidine belongs to a new class of alpha2-receptor agonists containing a 4-substituted imidazole ring with, high selectivity towards 2-adrenoreceptors. Receptors affected by catecholamine neurotransmitters, such as norepinephrine and epinephrine, are termed adrenergic receptors (or adrenoceptors) and can be divided into alpha- and beta-subclasses. The alpha2-adrenoreceptors are involved in the autoinhibitory mechanism of neurotransmitter release and play a significant part in the regulation of hypertension (high blood pressure), bradycardia (reduced heartbeat rate) and even regulation of alertness and analgesia (reduced sensitivity to pain). Medetomidine has been studied in human clinical trials and has also been used as anaesthetics for animals with the (S)-enantiomer, Dexmedetomidine, being the active component.

Nanoparticles are nanometer-sized metallic and semiconducting particles that have recently been the subject of extensive research in the field of nanoscale materials. Nanoparticles have potential applications in many diverse fields. These applications include: nanoscale electronic devices, multifunctional catalysts, chemical sensors, and many biological applications such as biosensors, biological assays, transfection of organisms using gene-gun technology, and drug delivery.

Two important factors cause the properties of nanomaterials to differ significantly from other materials: increased relative surface area, and quantum effects. These factors can change or enhance properties such as reactivity, strength and electrical characteristics. As a particle decreases in size, a greater proportion of atoms are found at the surface compared to those inside. For example, a particle of size 30 nm has 5% of its atoms on its surface, at 10 nm 20% of its atoms, and at 3 nm 50% of its atoms. Thus nanoparticles have a much greater surface area per unit mass compared with larger particles. As growth and catalytic chemical reactions occur at surfaces, this means that a given mass of material in nanoparticulate form will be much more reactive than the same mass of material made up of larger particles (ref "Nanoscience and nanotechnologies: opportunities and uncertainties", Jul. 29, 2004, Royal academy of Engineering, UK).

Also the use of nanoparticles in paints, for antifouling and other uses, has been previously discussed but then in order to change the structure of the painted surface to be able to be for example thinner, or smoother for less fouling on marine structures (ref "Environmental applications and impacts of nanotechnology 8 Dec. 2003, proceedings from the Royal academy of Engineering, UK) or rougher surfaces for less fouling but not the concept of using nanoparticles for the specific bindings of biocides disclosed in the present invention.

It is therefore an object of the invention to provide a method and product for use in antifouling products such as paints, using nanoparticles to bind the biocides. Other objects and advantages will be more fully apparent from the following disclosure and appended claims.

SUMMARY OF THE INVENTION

The invention herein relates to the method and use in an antifouling paint of an imidazole containing compound, such as Medetomidine, bound to metal nanoparticles that specifically and efficiently impede settlement of for example barnacles on aquatic structures. Medetomidine was surprisingly found to adsorb strongly to metal nanoparticles, a feature of particular interest in attempts to develop an efficient antifouling surface and improve the performance of antifouling paints with regard to distributed fixation of the biocide in the paint matrix for even release and effect in hindering for example barnacle colonization. Other biocide systems can be used with the same metal nano particle interaction for even release in other paints than marine antifouling paint.

BRIEF DESCRIPTION OF THE DRAWINGS

FIG. 1 shows the chemical structures of the investigated antifouling agents: a) Chlorothalonil, b) Dichlofluanid (N'-dimethyl-N-phenylsuphamide), c) SeaNine (SeaNine™ (4,5-dichloro-2-n-octyl-3(2H)-isothiazolone), Rohm and Haas Company, Philadelphia, Pa.), d) Irgarol (2-methylthio-4-tert-butylamino-6-cyclopropylamino-s-triziane), e) Diuron (3-(3, 4-dichlorophenyl)-1,1-dimethylurea), DuPont Agricultural Products Wilmington, Del., and f) Tolylfluanid (N-(Dichlorofluoromethylthio)-N',N'-dimethyl-N-p-tolylsufamide).

FIG. 2a) and FIG. 2b) show plots of the fraction adsorbed antifouling agent (Medetomidine, Chlorothalonil, Dichlofluanid, SeaNine, Irgarol, Diuron, and Tolylfluanid) versus surface area ($m^2$) of FIG. 2a) being ZnO and FIG. 2b) being CuO nanoparticles, in o-xylene.

DETAILED DESCRIPTION OF THE INVENTION AND PREFERRED EMBODIMENTS THEREOF

Figure 3:
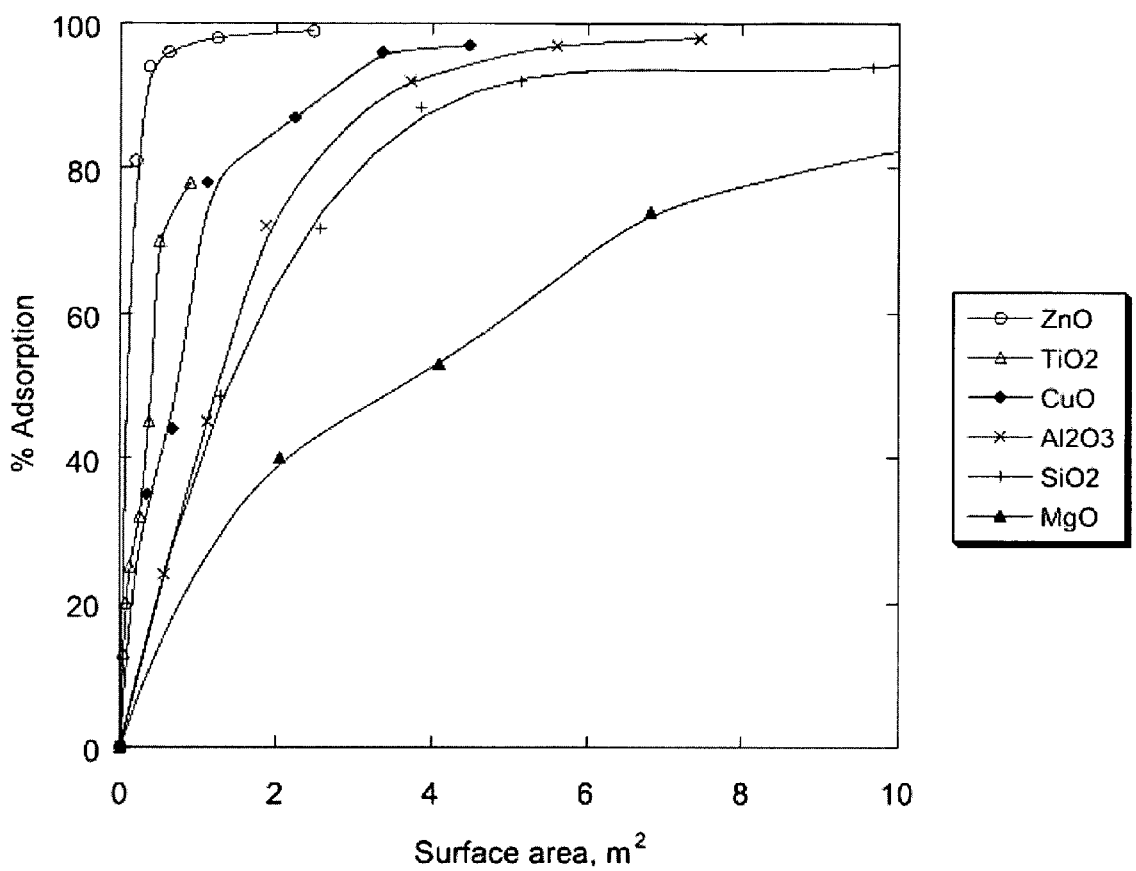
FIG. 3 is a plot of the fraction adsorbed Medetomidine versus surface area (m2) of ZnO, CuO, $Al_2O_3$, MgO, $TiO_2$, $Co_3O_4$ nanoparticles and CuO (5 µm), in o-xylene.

Recent studies, not yet published, have shown that nanoparticles, such as copper(II) and zinc(II) Oxide (33 and 53 nm in diameter, respectively) can be utilized in order to sustain a controlled release of, for example, the antifouling agent Medetomidine. The use of nanoparticles is of interest due to their tremendously large specific surface area (ratio between surface area and particle volume). The CuO and ZnO particle generates specific surface areas of 29 and 21 $m^2 \cdot g-1$, respectively.

When mixing CuO and ZnO nanoparticles with Medetomidine and other antifouling agents such as Chlorothalonil, Dichlofluanid, SeaNine, Irgarol, Diuron, and Tolylfluanid, in o-xylene, a considerable difference in interaction is observed. Large fractions of Medetomidine are adsorbed already at low particle concentrations, in particular when employing ZnO. This allows the possibility to design a paint system containing low amounts of both Medetomidine and nanoparticles in order to restrict the diffusional motion of antifouling agent through the paint film. The adsorption of Medetomidine is highly favoured in comparison to the other antifouling agents listed above. The antifouling agents listed above exhibit one common feature; nitrogen is present in all compounds either as secondary or tertiary amine, nitrile group or in a heterocyclic ring. However, the study implies that the imidazole moiety of Medetomidine has the optimal geometry for adsorption onto the particle surfaces.

In order to investigate the significance of a large surface area, the interaction of Medetomidine and various metal oxide nanoparticles (ZnO, CuO, $Al_2O_3$, MgO, $TiO_2$, $Co_3O_4$) and a micrometer sized-particle, CuO (5 µm) has been studied. When substituting a nanoparticle with a micrometer sized particle, the Medetomidine adsorption appears to be negligible. These results show the importance of large surface areas with regard to Medetomidine adsorption onto particle surfaces.

One object of this invention is to create an antifouling method requiring decreased biocide dose which is ecologically and economically advantageous. In order to improve the performance and to reduce the effect on the environment, it is important to have a proper control of the release of the antifouling substance from the paint film. The Medetomidine molecule bound to nanosized metal oxide is a compound that leaks out of the paint into water in a controlled fashion. The Medetomidine molecule bound to nanosized metal oxide has excellent dispersion stability because of its large size, compared to the Medetomidine particle alone. By size property the Medetomidine-metal oxide particles are stationary in a SPC paint film and don't leak out into the water. As a consequence the concentration of antifouling particles in the paint film remains homologous during "lifetime".

Metal nanoparticles provide a great number of binding sites for Medetomidine and a high amount of Medetomidine can be bound. As a result the concentration of Medetomidine will be equal in the entire paint film. Thereby the desorbtion will be at a uniform level and a minimum amount of Medetomidine will be needed to achieve antifouling effects. Another consequence is that the total surface area of nanoparticles is enough to adsorb all of the Medetomidine and there will be no waste of the biocide.

When exposed to water the Medetomidine in the surface layer dissociates from the metal oxide and desorbs from the surface. A surface-active compound in antifouling paint is thus likely to have a greater impact on settlements of barnacle larvae than a compound leaking out of the paint into the water since surface activity will increase the concentration close to the surface.

Due to a broad surface area relative to its size metal nanoparticles provide a great number of binding sites for biocides. As a consequence the amount of metal oxide can be decreased and thereby the negative effect on the environment achieved from metal oxides.

Medetomidine in accordance with the invention is comparatively harmless compared with the toxic substances presently used in ship hull paints. Indeed, Medetomidine in accordance with the invention is so harmless that it is approved as pharmaceutical preparations for internal use. Medetomidine is also biodegradable so there is less bioaccumulation of this substance, and it is therefore ecologically safer than many existing antifouling compounds. Other imidazole containing biocides, such as for example anti fungal Micronazole can be used.

Example 1

Study of the Interaction Between Various Nano Particles and Biocides

Materials and Methods

To 50 ml of the solvent o-xylene, the biocide was added at a total concentration of 50 mM. Nano-particles (Sigma-Aldrich Sweden AB, Stockholm, Sweden) were then added in relevant concentrations according to the test protocol and after each addition the concentration of non-adsorbed Medetomidine (Orion Pharma, Helsinki, Finland) was measured with a standard HPLC-UV technique. The UV-absorbance maximum of Medetomidine was, from the literature, found to be 220 nm. Prior to the HPLC analysis the UV-absorbance maximum was investigated in order to verify the value given from the literature using a UV-spectrometer (GBC 920 UV/visible spectrometer, Scientific Equipments Ltd., Victoria, Australia).

The samples were analysed on a HPLC-UV system consisting of a Merck-Hitachi L-6200 pump (Merck-Hitachi, Darmstadt, Germany), a Supelco Discovery® (Sigma-Aldrich Sweden AB, Stockholm, Sweden) C18 (25 cm×4.6 mm, 5 m) column fitted with a prefilter (0.5 µm) and a Spectra-Physics Spectra 100 UV (Spectra-Physics Inc, Irvine Calif., USA) operating at 220 nm. The mobile phase was MilliQ-water:Acetonitrile (0.1% TFA v/v (mobile phase A): 0.1% TFA v/v (mobile phase B)) run over a gradient (6% B for two min then an increase up to 60% B in 15 min, a further increase up to 100% B in 3 min and then isocratic for 3 min before returning to the starting values in 2 min) at a flow rate of 10 ml/min. The peak separation was monitored by UV (220 nm). Manual injections of 100 micro-liter were made and the data was collected and integrated using the Millenium software (version 3.20, 1999)(Waters Inc, Milford Mass., USA).

Results

When mixing CuO and ZnO nanoparticles with Medetomidine and other antifouling agents such as Chlorothalonil, Dichlofluanid, SeaNine, Irgarol, Diuron, and Tolylfluanid, in o-xylene (see FIGS. 1, 2a) and 2b), a considerable difference in interaction is observed. Large fractions of Medetomidine are adsorbed already at low particle concentrations, in particular when employing ZnO. This allows the possibility to design a paint system containing low amounts of both Medetomidine and nanoparticles in order to restrict the diffusional motion of antifouling agent through the paint film. The adsorption of Medetomidine is highly favoured in comparison to the other antifouling agents listed above. The antifouling agents listed above exhibit one common feature; nitrogen is present in all compounds either as secondary or tertiary amine, nitrile group or in a heterocyclic ring. However, the study implies that the imidazole moiety of Medetomidine has the optimal geometry for adsorption onto the particle surfaces.

It should be noted that while Medetomidine exhibited the best adsorption, some of the other compounds, particularly SeaNine, as well as diuron and igarol, also exhibited adsorption in this study.

Example 2

Study of the Interaction Between Various Sizes of Particles and Biocides

Materials and Methods

The different nanoparticles used (ZnO, CuO, $Al_2O_3$, MgO, $TiO_2$, $CO_3O_4$) were bought from Sigma (Sigma-Aldrich Sweden AB, Stockholm, Sweden) and used without further purification. 50 ml of o-xylene was added to a beaker to which 50 mM of Medetomidine (Orion Pharma, Helsinki, Finland) was added. Nanoparticles were then added and after each addition the amount of free Medetomidine was measured with HPLC-UV (as in example 1 above).

Results

Figure 4:
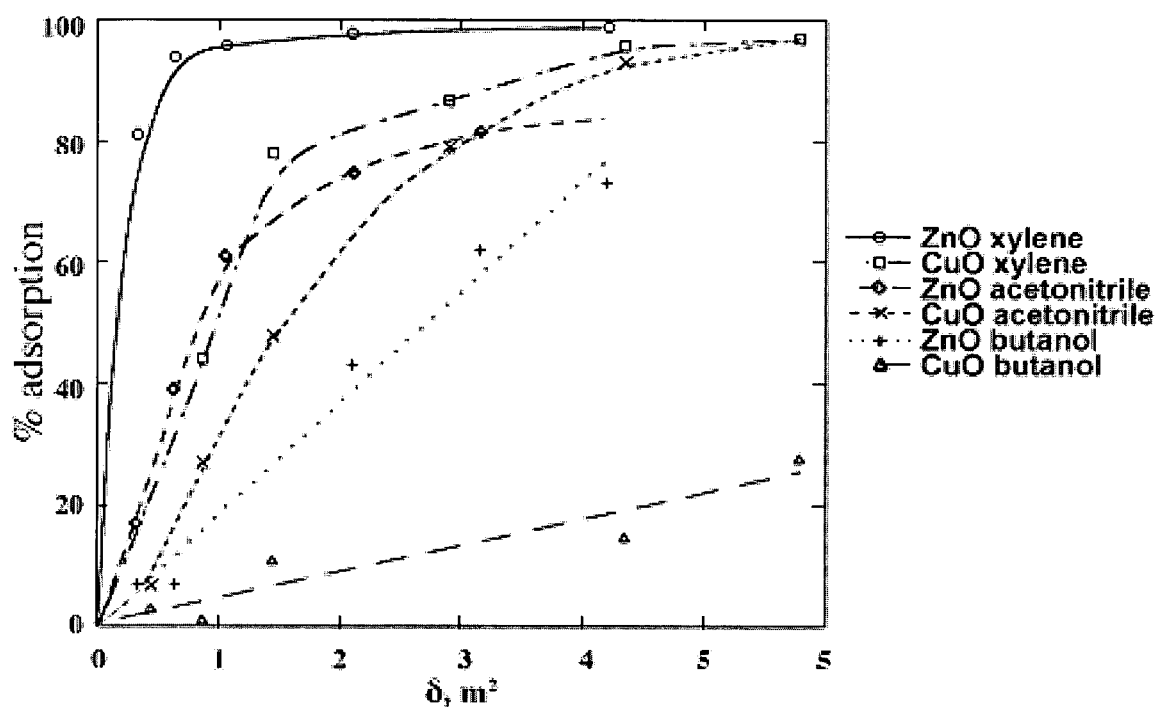
FIG. 4 is a plot of the fraction adsorbed Medetomidine plotted versus surface area ($m^2$) of ZnO and CuO, nanoparticles in o-xylene, acetonitrile and butanol.

In order to investigate the significance of a large surface area, the interaction of Medetomidine and various metal oxide nanoparticles (ZnO, CuO, $Al_2O_3$, MgO, $TiO_2$, $CO_3O_4$) and a micrometer sized particle, CuO (5 μm) has been studied (see FIGS. 3 and 4). When substituting a nanoparticle with a micrometer sized particle the Medetomidine adsorption appears to be negligible. These results show the importance of large surface areas with regard to Medetomidine adsorption onto particle surfaces.

Example 3

Study of the Release Rate of a Biocide from Nano Particles

Materials and Methods

The paint chosen for these studies was a self-polishing paint with xylene as the solvent, the SPC Lefant marine paint from Lotréc AB (Lindingo, Sweden), To one liter paint a 50 ml solution containing 10 g of nano particles (CuO and ZnO) (Sigma-Aldrich Sweden AB, Stockholm, Sweden) and surface adsorbed Medetomidine (Orion Pharma, Helsinki, Finland) or SeaNine (Rhome & Haas, Philadelphia, Pa., USA) was added and mixed under vigorous stirring for five minutes. Triplicate samples were prepared and painted using a paint applicator in order to assure a homogeneously thick paint film which in this case was 200 micrometer. The painted plates were 10×10 cm and placed in artificial seawater for a period of 8 weeks.

Results

Figure 5:
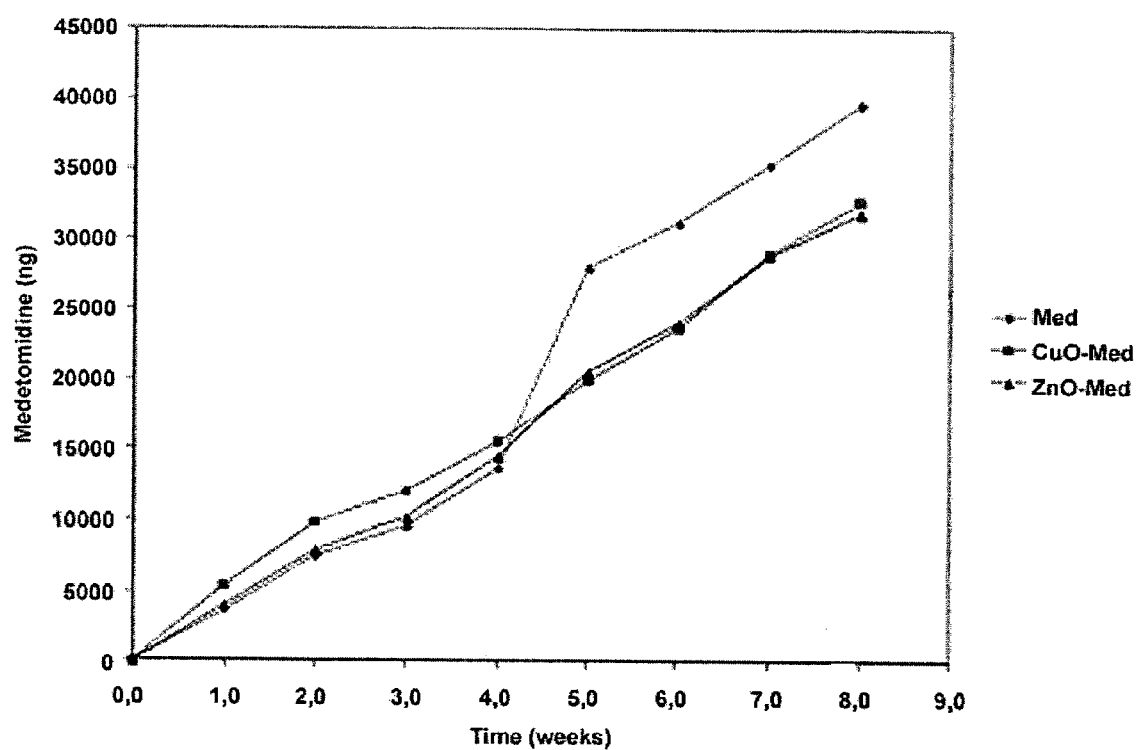
FIG. 5 is a plot of the amount released Medetomidine (ng) versus time (weeks) for CuO and ZnO nanoparticles-Medetomidine modified paints and Medetomidine modified marine paint.
Figure 6:
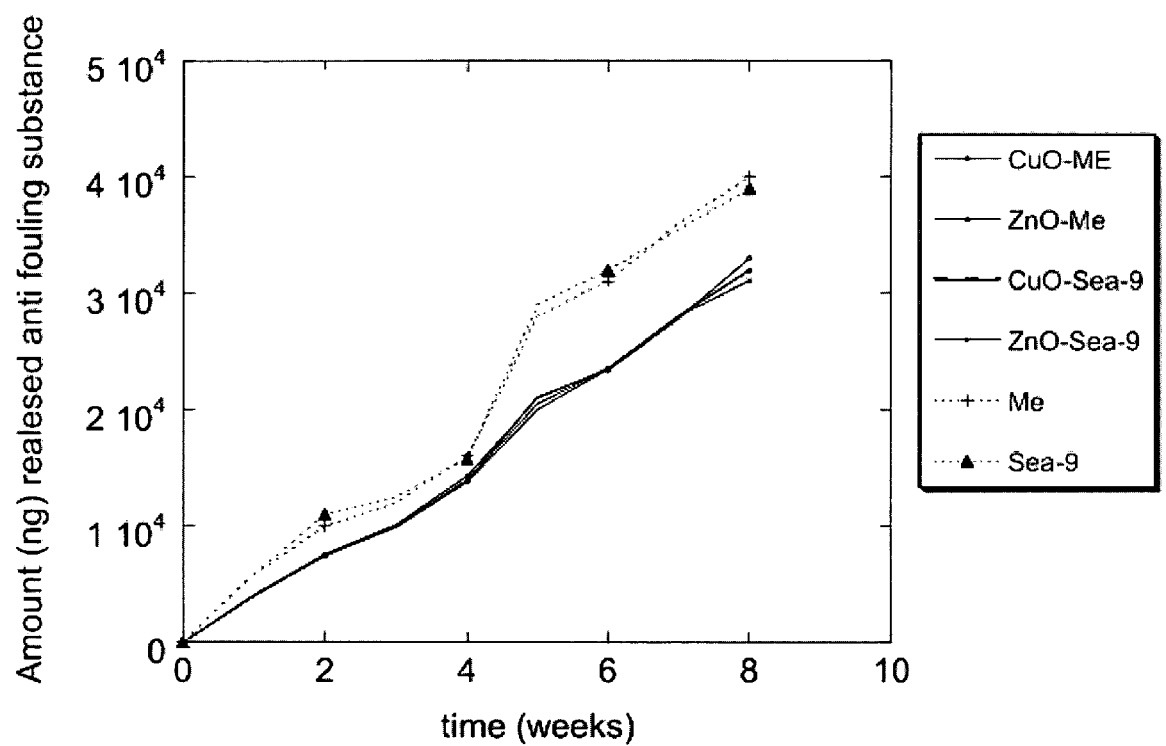
FIG. 6 is a plot of the amount released Medetomidine and SeaNine (ng) versus time (weeks) for CuO and ZnO nanoparticles-Medetomidine or nanoparticles-SeaNine and Medetomidine, SeaNine modified marine paints.

The Medetomidine-nanoparticle interaction (Medetomidine-CuO and Medetomidine-ZnO) has also been employed for release rate studies (see FIG. 5). After eight weeks the Medetomidine-nanoparticle modified paints generated a 20% decrease in released amount of Medetomidine in comparison to the paint with Medetomidine as single additive. The results for the SeaNine-nanoparticle interaction are showed in FIG. 6, which demonstrates a similar decrease in release as with the Medetomedine-nanoparticle combination.

Example 4

Manufacture of a Paint for Anti-Fouling Using Nano Particles to Bind a Biocide

As one example of a Medetomidine modified paint a typical paint chosen for these studies contained Xylene as the main solvent (the SPC Lefant marine paint from Lotrec AB, Lindingo, Sweden), In order to prepare the paint containing both nanoparticles and biocides these two components were first mixed in a solvent allowing for very strong adsorption of biocide, e.g. xylene. Typically, 10 gram of nanoparticle was stirred in 50 ml of xylene (using a simple magnetic stirrer) together with a maximum of 10% excess of non-adsorbed Medetomidine, After complete adsorption (typically a few minutes of mixing) the solution was slowly added into the paint under quite vigorous stirring (Stirring was carried with a propeller-like shearer working at approximately 0.5-2 Hz)until the paint became homogeneous which took typically 5-10 minutes depending on the stirring rate.

Nanoparticles were bought from Sigma (Sigma-Aldrich Sweden AB, Stockholm, Sweden) and used without further purification Medetomidine was bought from Orion Pharma, Helsinki, Finland.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A product for preventing marine biofouling of a substrate by a marine biofouling organism, comprising a protective paint containing a compound selected from the group consisting of Chlorothalonil, N'-dimethyl-N-phenylsuphamide; 4,5-dichloro-2-n-octyl-3(2H)-isothiazolone: 2-methylthio-4-tert-butylamino-6-cyclopropylamino-s-triziane; 3-(3,4-dichlorophenyl)-1,1-dimethylurea; N-(Dichlorofluoromethylthio)-N',N'-dimethyl-N-p-tolylsufamide and 2-(p-chlorophenyl)-3-cyano-4-bromo-5-trifluoromethyl pyrrole bound to metal oxide nanoparticles.

2. The product for preventing marine biofouling according to claim 1, wherein the compound bound to metal oxide nanoparticles is 2-(p-chlorophenyl)-3-cyano-4-bromo-5-trifluoromethyl pyrrole.

3. The product for preventing marine biofouling according to claim 1, wherein the metal oxide nanoparticles are selected from the group consisting of CuO, ZnO, $TiO_2$, $Al_2O_3$, $SiO_2$, and MgO.

4. The product for preventing marine biofouling according to claim 2, wherein the product further comprises Medetomidine.

5. The product for preventing marine biofouling according to claim 2, wherein the metal oxide nanoparticles are CuO.

6. The product for preventing marine biofouling according to claim 2, wherein the metal oxide nanoparticles are ZnO.

* * * * *